United States Patent [19]

Dembinski

[11] 4,374,132
[45] Feb. 15, 1983

[54] PLASMA URIC ACID LOWERING METHOD

[75] Inventor: Joan R. Dembinski, Albany, N.Y.

[73] Assignee: Sterling Drug Inc., New York, N.Y.

[21] Appl. No.: 101,628

[22] Filed: Dec. 10, 1979

[51] Int. Cl.³ .............................................. A61K 31/58
[52] U.S. Cl. .................................................... 424/241
[58] Field of Search ........................................ 424/241

[56] References Cited

U.S. PATENT DOCUMENTS 3,966,926  6/1976  Potts ..................................... 424/241

*Primary Examiner*—Elbert L. Roberts
*Attorney, Agent, or Firm*—Theodore C. Miller; B. Woodrow Wyatt

[57] ABSTRACT

A method of lowering plasma uric acid using 17β-hydroxy-4,4,17α-trimethyl-5-androsteno[2,3-d]isoxazole is disclosed.

1 Claim, No Drawings

PLASMA URIC ACID LOWERING METHOD

BACKGROUND OF THE INVENTION

1. Field of the Invention

The invention relates to a method of lowering plasma uric acid using a steroid.

2. Description of the Prior Art

Throughout this specification the term "uric acid" is intended to include salts of uric acid (urates), which occur together with uric acid in the plasma, as well as uric acid itself.

17β-Hydroxy-4,4,17α-trimethyl-5-androsteno[2,3-d]-isoxazole having the structural formula

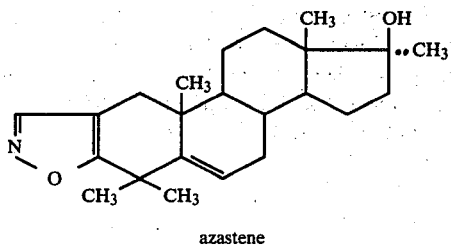

azastene is described by Example 22 of U.S. Pat. No. 3,135,743, which states that it "was found to possess a blocking action on the adrenal response to ACTH in castrated male rats". The current Chemical Abstracts name of the compound is (17β)-4,4,17-trimethylandrosta-2,5-dieno[2,3-d]isoxazol-17-ol and the United States adopted name is azastene. A method for disrupting pregnancy using azastene is described by U.S. Pat. No. 3,966,926.

Plasma uric acid lowering agents are used in the treatment of gout (AMA Drug Evaluations, Third Edition, Chapter 24, pp. 364–373, 1977) and are of two types according to their mode of action. Probenecid and sulfinpyrazone are of one type which increases renal excretion of uric acid (uricosuric agents). Allopurinol is of the other type which decreases formation of uric acid. These agents are not effective in treating acute gout but are used in treating chronic tophaceous gout.

Colchicine and the antiinflammatory-analgesic drugs, indomethacin, phenylbutazone and oxyphenbutazone, are used in treating the pain and tenderness of acute gout. Corticotropin (ACTH) and the adrenal corticosteroids are also rarely used for the same purpose, but none of these agents affects plasma uric acid concentration.

Nor are any other steroids known to affect plasma uric acid concentration.

SUMMARY OF THE INVENTION

The invention is the method of treating a person having abnormally high plasma uric acid concentration which comprises administering to the person an amount of 17β-hydroxy-4,4,17α-trimethyl-5-androsteno[2,3-d]isoxazole effective in lowering the plasma uric acid concentration.

DETAILED DESCRIPTION OF THE INVENTION INCLUSIVE OF THE PREFERRED EMBODIMENTS

In clinical trial of azastene at doses from 62.5 to 2000 milligrams, there resulted a surprising and unexpected dose related reduction of the plasma uric acid concentration.

The results of a study in which forty women participated are shown in Table I. Twelve women were given placebo and the remaining twenty-eight were given azastene orally in doses ranging from 62.5 to 2000 milligrams twice a day for five days. Blood samples were taken prior to medication, within twenty-four hours of the last medication, and about one month after the last medication, and plasma uric acid concentrations were determined by a phosphotungstate reduction method.

TABLE I

| Azastene Dose (mg. b.i.d.) | Plasma Uric Acid Concentration (mg./dl.) | | |
|---|---|---|---|
| | Pre-medication | Medication | Post-medication |
| Placebo | 4.4 | 3.7 | 5.4 |
| | 4.2 | 3.9 | 3.8 |
| | 5.2 | 4.8 | 2.9 |
| | 3.5 | 2.9 | 3.7 |
| | 3.4 | 3.5 | 2.4 |
| | 3.7 | 3.7 | 4.2 |
| | 3.9 | 3.3 | 4.6 |
| | 5.2 | 4.2 | 4.3 |
| | 3.7 | 3.4 | 3.8 |
| | 4.1 | 3.6 | 4.3 |
| | 5.1 | 4.1 | 5.2 |
| | 4.4 | 3.1 | 4.5 |
| 62.5 | 5.4 | 4.6 | 6.3 |
| | 3.6 | 3.0 | 3.5 |
| | 6.2 | 4.9 | 5.3 |
| | 3.7 | 3.1 | 3.3 |
| | 4.9 | 3.7 | 3.7 |
| 125 | 4.8 | 4.2 | 4.8 |
| | 4.2 | 2.8 | 4.3 |
| | 4.9 | 4.1 | 4.6 |
| | 2.8 | 1.6 | 8.3 |
| | 5.0 | 2.8 | 3.6 |
| 250 | 4.4 | 3.9 | 3.9 |
| | 4.1 | 1.9 | 3.6 |
| | 4.0 | 2.0 | 3.4 |
| | 4.3 | 2.3 | 3.8 |
| | 5.3 | 3.7 | 5.2 |
| 500 | 5.4 | 3.0 | 4.5 |
| | 4.8 | 2.2 | 5.0 |
| | 4.2 | 1.7 | 4.6 |
| | 4.0 | 3.4 | 4.5 |
| | 2.9 | 2.4 | 4.6 |
| 1000 | 5.4 | 1.9 | 4.2 |
| | 4.1 | 2.0 | 3.2 |
| | 3.1 | 1.7 | 3.7 |
| | 5.4 | 2.0 | 6.0 |
| 2000 | 5.1 | 1.3 | 4.3 |
| | 4.8 | 1.3 | 4.4 |
| | 4.4 | 1.4 | 3.7 |
| | 5.9 | 2.1 | 4.8 |

The results shown in Table I were subjected to statistical analysis and are summarized as means with standard errors in Table II. The mean of pre-medication plasma uric acid concentrations for all forty patients is 4.45 milligrams per deciliter with a standard deviation of 0.81 milligrams per deciliter. Thus, any medication concentration less than 2.83 milligrams per deciliter is two standard deviations less than the mean. Based on two-tailed "t" tests the mean medication concentrations at the 250, 500 and 1000 milligram doses are statistically different from the mean pre-medication concentration with $p < 0.01$, and the mean medication concentration at the 2000 milligram dose is statistically different from the mean pre-medication concentration with $p < 0.001$.

TABLE II

| Azastene Dose (mg. b.i.d.) | Number of Patients | Plasma Uric Acid Concentration Mean ± Standard Error (mg./dl.) | | |
|---|---|---|---|---|
| | | Pre-Medication | Medication | Post-Medication |
| Placebo | 12 | 4.23 ± 0.19 | 3.68 ± 0.15 | 4.09 ± 0.25 |
| 62.5 | 5 | 4.76 ± 0.05 | 3.86 ± 0.38 | 4.42 ± 0.59 |
| 125 | 5 | 4.34 ± 0.41 | 3.10 ± 0.48 | 5.12 ± 0.82 |
| 250 | 5 | 4.42 ± 0.23 | 2.76 ± 0.43 | 3.98 ± 0.32 |
| 500 | 5 | 4.26 ± 0.42 | 2.54 ± 0.30 | 4.64 ± 0.09 |
| 1000 | 4 | 4.50 ± 0.56 | 1.90 ± 0.07 | 4.28 ± 0.61 |
| 2000 | 4 | 5.05 ± 0.32 | 1.53 ± 0.19 | 4.30 ± 0.23 |

The pre-medication and post-medication uric acid concentrations shown in Tables I and II are in the normal range. However, in practice the invention is intended to be used in persons having abnormally high uric acid concentrations including those suffering from gout, those having asymptomatic hyperurecemia and those having secondary hyperurecemia (AMA Drug Evaluations, ibid., p. 365). The preferred dose of azastene for the purposes of the invention is anticipated to be from about 100 to about 500 milligrams twice a day, but the effective dose for the particular person will have to be determined by the prescribing physician.

Azastene is prepared for use by incorporating it in an inert pharmaceutical carrier. The formulation is prepared by dissolving or suspending the steroid in a pharmaceutically acceptable liquid vehicle, e.g. aqueous ethanol, glycol, cottonseed oil solution or oil-water emulsion, gum tragacanth suspension, or the like; or by incorporating the steroid in unit dosage form as tablets or capsules either alone or in combination with conventional adjuvants, e.g. lactose, starch, silicon dioxide, talc, gum acacia, magnesium stearate, calcium carbonate and the like.

I claim:

1. The method of treating a person other than a pregnant female person having an abnormally high plasma uric acid concentration which comprises administering to the person an amount of 17$\beta$-hydroxy-4,4,17$\alpha$-trimethyl-5-androsteno[2,3-d]isoxazole effective in lowering the plasma uric acid concentration.

* * * * *